(12) United States Patent
Miller (10) Patent No.: US 11,583,232 B2
(45) Date of Patent: Feb. 21, 2023

(54) CATHETER INCLUDING A PLURALITY OF SENSORS

(71) Applicant: Covidien LP, Mansfield, MA (US)

(72) Inventor: David J. Miller, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 378 days.

(21) Appl. No.: 16/854,592

(22) Filed: Apr. 21, 2020

(65) Prior Publication Data

US 2021/0186428 A1    Jun. 24, 2021

Related U.S. Application Data (60) Provisional application No. 62/952,776, filed on Dec. 23, 2019.

(51) Int. Cl.
*A61B 5/00* (2006.01)
*A61B 5/03* (2006.01)
(Continued)

(52) U.S. Cl.
CPC .............. *A61B 5/6852* (2013.01); *A61B 5/01* (2013.01); *A61B 5/036* (2013.01); *A61B 5/0538* (2013.01);
(Continued)

(58) Field of Classification Search
CPC ......... A61B 5/6852; A61B 5/01; A61B 5/036; A61B 5/0538; A61B 5/1032; A61B 5/11; A61B 5/14503; A61B 5/14539; A61B 5/14542; A61B 5/14546; A61B 5/205; A61B 5/208; A61B 5/6858; A61B 5/14507; A61B 5/6853; A61B 2562/06; A61B 5/6874; A61B 5/204; A61B 2562/0219; A61B 5/202; A61B 5/201; A61L 29/041; A61L 29/085; A61L 29/14;
(Continued)

(56) References Cited

U.S. PATENT DOCUMENTS 1,870,942 A     8/1932  Beatty
5,389,217 A  *  2/1995  Singer .................. A61B 5/6853
                                                          204/415
(Continued)

FOREIGN PATENT DOCUMENTS

WO    2002/096286 A1    12/2002
WO    2014/043650 A2     3/2014
(Continued)

OTHER PUBLICATIONS

International Search Report and Written Opinion of International Application No. PCT/US2020/065353, dated Mar. 10, 2021, 15 pp.
(Continued)

*Primary Examiner* — May A Abouelela
(74) *Attorney, Agent, or Firm* — Shumaker & Sieffert, P.A.

(57) ABSTRACT

In some examples, a medical device includes an elongated body defining an inner lumen. The medical device further includes an anchoring member and a first sensor at a proximal portion of the elongated body, and a second sensor at a distal portion of the elongated body or distal to a distal end of the elongated body. The second sensor is configured to sense a substance of interest and the elongated body comprises a material that is a substantially non-permeable to the substance of interest.

28 Claims, 7 Drawing Sheets

(51) Int. Cl.

| | |
|---|---|
| *A61B 5/145* | (2006.01) |
| *A61B 5/0538* | (2021.01) |
| *A61B 5/20* | (2006.01) |
| *A61B 5/11* | (2006.01) |
| *A61L 29/04* | (2006.01) |
| *A61L 29/14* | (2006.01) |
| *A61B 5/103* | (2006.01) |
| *A61B 5/01* | (2006.01) |
| *A61L 29/08* | (2006.01) |
| *A61M 25/00* | (2006.01) |
| *A61M 25/01* | (2006.01) |

(52) U.S. Cl.
CPC .............. *A61B 5/1032* (2013.01); *A61B 5/11* (2013.01); *A61B 5/14503* (2013.01); *A61B 5/14539* (2013.01); *A61B 5/14542* (2013.01); *A61B 5/14546* (2013.01); *A61B 5/205* (2013.01); *A61B 5/208* (2013.01); *A61B 5/6858* (2013.01); *A61L 29/041* (2013.01); *A61L 29/085* (2013.01); *A61L 29/14* (2013.01); *A61B 5/14507* (2013.01); *A61B 5/6853* (2013.01); *A61B 2562/06* (2013.01); *A61M 25/0017* (2013.01); *A61M 25/0147* (2013.01); *A61M 2025/0004* (2013.01)

(58) Field of Classification Search
CPC .......... A61M 25/0017; A61M 25/0147; A61M 2025/0004; A61M 25/04
See application file for complete search history.

(56) References Cited

U.S. PATENT DOCUMENTS

| | | | |
|---|---|---|---|
| 6,238,339 | B1 | 5/2001 | Fiddian-Greene et al. |
| 6,602,243 | B2 | 8/2003 | Noda |
| 9,655,555 | B2 | 5/2017 | Burnett et al. |
| 9,662,058 | B2 | 5/2017 | Burnett et al. |
| 10,349,873 | B2 | 7/2019 | Kamath et al. |
| 10,391,275 | B2 | 8/2019 | Burnett et al. |
| 10,542,923 | B2 | 1/2020 | Chang et al. |
| 2006/0178571 | A1* | 8/2006 | Barnett ................. A61B 5/202 600/311 |
| 2009/0105799 | A1 | 4/2009 | Hekmat et al. |
| 2013/0066166 | A1* | 3/2013 | Burnett ................ A61B 5/7278 600/301 |
| 2016/0310711 | A1 | 10/2016 | Luxon et al. |
| 2017/0136209 | A1* | 5/2017 | Burnett .................. A61M 1/84 |
| 2019/0069831 | A1 | 3/2019 | Kuck et al. |
| 2019/0126006 | A1 | 5/2019 | Rehm et al. |
| 2019/0150801 | A1 | 5/2019 | Suehara et al. |
| 2019/0321588 | A1 | 10/2019 | Burnett et al. |
| 2019/0343445 | A1 | 11/2019 | Burnett et al. |
| 2020/0022636 | A1 | 1/2020 | Suehara et al. |

FOREIGN PATENT DOCUMENTS

| | | |
|---|---|---|
| WO | 2014/210453 A2 | 12/2014 |
| WO | 2019/038732 A1 | 2/2019 |
| WO | 2019/115809 A1 | 6/2019 |

OTHER PUBLICATIONS

"Clarity RMS", retrieved from https://www.renalsense.com/clarity-rms/, Feb. 4, 2020, 6 pp.
Avulova et al., "Do Foley Catheters Adequately Drain the Bladder? Evidence from CT Imaging Studies", . Int Braz J Urol., May-Jun. 2015, vol. 41(3), pp. 552-555.
Parker, "Urinary catheter management: minimizing the risk of infection," Infection Control: Series Sponsored by Regent Medical, British Journal of Nursing, vol. 8, No. 9, Apr. 1999 1:6, 332-339.
Zhang et al., "The Permeability Characteristics of Silicone Rubber", Society for the Advancement of Material and Process Engineering, Coatings and Sealants Section, Nov. 6-9, 2006, 10 pp.
ASTM International, "Standard Performance Specification for Foley Catheter", F623-19, Mar. 1, 2019, 10 pp.
U.S. Appl. No. 16/840,150, filed Apr. 3, 2020, naming inventor David J Miller.
International Preliminary Report on Patentability from International Application No. PCT/US2020/065353, dated Jul. 7, 2022, 9 pp.
Notice of Allowance from U.S. Appl. No. 16/840,150 dated Sep. 23, 2022, 8 pp.
Response to Office Action dated Jun. 16, 2022 from U.S. Appl. No. 16/840,150, filed Sep. 7, 2022, 9 pp.
Office Action from U.S. Appl. No. 16/840,150, dated Jun. 16, 2022, 8 pp.

* cited by examiner

CATHETER INCLUDING A PLURALITY OF SENSORS

This application claims the benefit of U.S. Provisional Application No. 62/952,776, filed on Dec. 23, 2019, and entitled, "CATHETER INCLUDING A PLURALITY OF SENSORS." The entire content of U.S. Provisional Application No. 62/952,776 is incorporated herein by reference.

TECHNICAL FIELD

This disclosure relates to medical devices, more particularly, to catheters.

BACKGROUND

Medical devices, such as catheters, may be used to assist a patient in voiding their bladder. In some instances, such catheters may be used during and/or after surgery. In the case of using a catheter to assist a patient in voiding their bladder, a Foley catheter is a type of catheter that may be used for longer time periods than a non-Foley catheter. Some Foley catheters are constructed of silicon rubber and include an anchoring member, which may be an inflatable balloon, that may be expanded in a patient's bladder to serve as an anchor so a proximal end of the catheter does not slip out of the patient's bladder.

SUMMARY

In general, this disclosure describes a medical device, such as a catheter (e.g., a Foley catheter), that includes a plurality of sensors at different locations which may be along a length of an elongated body of the medical device. One or more sensors (referred to herein as a "first sensor") are positioned at a proximal portion of the elongated body and one or more sensors (referred to herein as a "second sensor") are positioned at a distal portion of the elongated body. As used herein, proximal is used as defined in Section 3.1.4 of ASTM F623-19, Standard Performance Specification for Foley Catheter. That is, the proximal end of the medical device is the end closest to the patient. The distal end is therefore the end furthest from the patient.

The second sensor is configured to sense one or more substances of interest, and a portion or an entirety of the elongated body comprises a material that is substantially non-permeable (e.g., non-permeable or nearly non-permeable) to the substances of interest to help minimize loss and/or contamination of the substances of interest as the fluid in which the substances of interest are present propagates through a lumen of the elongated body to the second sensor. The second sensor may also be configured to sense a property of the fluid. In this way, the medical device is configured to enable a sensor to sense the substance of interest despite being positioned relatively far away from the fluid source, such as a bladder. In some examples, the first sensor and second sensor are configured to sense different parameters. As used herein, "sense" may include "detect" and/or "measure."

In some examples, the catheter includes an anchoring member configured to anchor the elongated body within the patient, such as within a bladder of the patient. In some examples, the anchoring member may an expandable structure such as an inflatable balloon or a non-balloon expandable structure, such as an expandable basket, expandable wings, an expandable mushroom shape, or other expandable structure.

In one example, this disclosure is directed to a device including an elongated body defining a lumen, the elongated body comprising a proximal portion and a distal portion, an anchoring member positioned at the proximal portion of the elongated body, a first sensor positioned at the proximal portion of the elongated body, and a second sensor positioned at the distal portion of the elongated body or distal to a distal end of the elongated body, the second sensor configured to sense a substance of interest, wherein the elongated body comprises a material that is a substantially non-permeable to the substance of interest.

In another example, this disclosure is directed to a method including sensing, by a first sensor positioned at a proximal portion of an elongated body of a medical device, a first parameter, the elongated body defining a lumen and further comprising an anchoring member on the proximal portion; and sensing, by a second sensor positioned at a distal portion of the elongated body or distal to a distal end of the elongated body, a second parameter, the second parameter comprising a substance of interest in a fluid in the lumen, wherein the elongated body comprises a material that is substantially non-permeable to the substance of interest.

In another example, this disclosure is directed to a Foley catheter including an elongated body defining a drainage lumen, the elongated body comprising a proximal portion and a distal portion, the proximal portion defining a drainage opening fluidically coupled to the drainage lumen; an anchoring member positioned at the proximal portion of the elongated body; a first sensor positioned at the proximal portion of the elongated body; and a second sensor positioned at the distal portion of the elongated body or distal to a distal end of the elongated body, the second sensor configured to sense a substance of interest, wherein the elongated body comprises a material that is a substantially non-permeable to the substance of interest, the material extending from the drainage opening to the second sensor.

The details of one or more examples are set forth in the accompanying drawings and the description below. Other features, objects, and advantages will be apparent from the description and drawings, and from the claims.

DETAILED DESCRIPTION

Acute kidney injury (AKI) is a complication that may occur after some medical procedures, such as some cardiac surgeries, e.g., coronary artery bypass grafting (CABG). AKI may also occur after other surgeries that are lengthy and involve significant blood loss or fluid shifts. For example, a surgery patient's body may alter where their blood is directed which may lead to hypoxia of a kidney. A cause of surgery-associated AKI is hypoxia of the kidneys, which may cause an inflammatory response in a kidney of the patient. This inflammatory response may cause degradation of renal function of the patient. The degradation of renal function may cause an accumulation of waste products in the bloodstream, which may delay the patient's recovery from the surgery and lead to more extended hospital stays and may even lead to further complications.

The present disclosure describes example medical devices that are configured to monitor kidney function of patients, such as patients who are undergoing or who have undergone such surgeries, which may help reduce occurrences of AKI. The medical device includes a plurality of sensors (e.g., two or more sensors) configured to sense different parameters of a fluid of interest, such as urine in the case of kidney function monitoring. While urine, bladders, and AKI are primarily referred to herein to describe the example medical devices, in other examples, the medical devices may be used with other target locations in a patient, such as intravascular locations, and to monitor substances of interest in fluids other than urine and/or other patient conditions other than kidney function.

Example sensed parameters that may be useful in determining the state of kidney function include, but are not limited to, any one or more of urine output (e.g. flow or volume), urine concentration, amount of dissolved oxygen in the urine (oxygen tension or uPO2), amount of dissolved carbon dioxide in the urine, urine pH, bladder or abdominal pressure, bladder temperature, urine color, urine creatinine, or motion from an accelerometer or other motion sensor. In some cases, it may be desirable to sense one or more of these parameters relatively close to the kidneys as possible because when sensors are positioned further away from the kidneys, the risk of introducing noise or losing signal strength increases and/or the risk of the concentration or integrity of a substance of interest in the fluid of interest changing prior to being sensed by the sensor may increase. For example, an electrical, optical or radio frequency signal representative of a parameter sensed close to the kidneys, may be affected by noise and/or loss of signal strength as the signal travels from a sensor close to the kidneys to a device that may process the signal and display information regarding the sensed parameter. For example, in the case of a Foley catheter, it may be desirable to sense one or more of these parameters at the proximal end of the Foley catheter (e.g., in the bladder of the patient). However, placing these sensors at the proximal end of the catheter may increase the size and stiffness of the catheter and, as a result, may undermine patient comfort or deliverability of the catheter. By design, a Foley catheter is made to be small and flexible, such that it can be inserted through the urethra and into the bladder of a patient.

The amount of dissolved oxygen in a patient's urine may be indicative of kidney function or kidney health. For example, dissolved oxygen in a patient's urine and bladder may correlate to perfusion and/or oxygenation of the kidneys, which is indicative of kidney performance. However, dissolved oxygen can be relatively difficult to measure. One way to measure dissolved oxygen is by fluorescence or luminescence lifetime sensor(s). The decay of glow is indicative of the level of oxygen in a patient's urine. To accurately measure the level of oxygen in a patient's urine, it may be desirable to take the measurement prior to any significant modification in the oxygen content in the urine, e.g., as close to the kidneys as possible. However, it may not be feasible to place a dissolved oxygen sensor at the proximal end of the catheter as doing so may increase cost, size, and flexibility of the catheter.

In accordance with examples of this disclosure, rather than integrating all of the desired sensors in the proximal portion of an elongated body of a medical device (e.g., the portion that is to be inserted into the bladder of the patient or otherwise introduced in a patient), such as a catheter, sensors may be positioned both at the proximal portion and at the distal portion of the elongated body or distal to the distal end of the elongated body. The distal portion of the elongated body may include, for example, the portion intended to remain outside of the patient when the proximal portion is introduced in the patient. To help minimize or even eliminate degradation and/or contamination of a substance of interest in the fluid of interest (e.g., urine) before the fluid reaches a sensor at a distal portion of the elongated body or distal to the distal end of the elongated body, a portion or an entirety of the elongated body comprises a material that is substantially non-permeable (e.g., non-permeable or nearly non-permeable) to the substances of interest.

In contrast to existing Foley catheters or other medical devices that are permeable to many substances of interest, the medical devices described herein enable a sensor to relatively accurately sense a substance of interest in a fluid despite being positioned relatively far away from the fluid source, such as a bladder. For example, some Foley catheters may include an elongated body made from silicone rubber, which is very porous to oxygen. Thus, using a dissolved oxygen sensor on the distal portion of such a Foley catheter to measure oxygen content in urine may result in erroneous or skewed measurements as the oxygen may dissipate from the urine through the walls of the Foley catheter as the urine travels from the bladder through the lumen at the proximal portion of the catheter to the sensor on the distal portion of the catheter and into a surrounding environment. Oxygen may also permeate the urine through the walls of the Foley catheter as the urine travels from the bladder through the lumen at the proximal portion of the catheter to the sensor on the distal portion of the catheter from the surrounding environment. For example, the oxygen may dissipate into or permeate from other tissues in the urinary tract and the atmosphere outside of the urinary tract. In some examples described herein, however, the elongated body of a Foley catheter comprises a material that is substantially non-permeable to oxygen, such that the amount of oxygen that dissipates or permeates through the walls of the Foley catheter is reduced relative to an elongated body that is formed from only silicone rubber.

The example medical devices described herein may be made of a plurality of materials, such that the medical devices may maintain flexibility and are configured to minimize the degradation of signals of interest. By locating sensors at the distal portion of the medical device (or distal to a distal end of the elongated body), the sensors may be larger, may rely upon relatively more electrical and/or optical connections and the medical device itself may be smaller and more flexible than it would have been had all the sensors been positioned at the proximal portion of the medical device.

The medical devices may be formed of any suitable materials, which may be selected based on the substance of interest. For example, in some examples, at least one of the plurality of materials from which a medical device is formed may be a material that is substantially non-permeable to substances of interest, such as oxygen or carbon dioxide. "Substantially non-permeable" may refer to being non-permeable or non-permeable to the extent permitted by manufacturing tolerances, and/or having a permeability such that a percentage of loss and/or increase of the substance of interest through the material (e.g., through walls of an elongated body including the material) is relatively minimal (e.g., less than or equal to 5% at a flow rate of 10 ml/hour). In some examples, the material that is substantially non-permeable to substances of interest extends along the entire length and perimeter of the elongated body. In other examples, the material that is substantially non-permeable to substances of interest extends along only part of the length and/or only part of the perimeter of the elongated body, such as only between the proximal portion of the elongated body and the distal sensor location. By constructing the medical device using a plurality of materials, at least one of which is substantially non-permeable to substance of interest, sensors may be positioned at the distal portion while providing more accurate sensor measurements and maintaining the flexibility and size of the catheter.

Any suitable materials may be used for the material that are substantially non-permeable to substances of interest, and the material can be selected based on the substance of interest. In "The Permeability Characteristics of Silicone Rubber," Haibing Zhang, Ph.D. and Andy Cloud, Society for the Advancement of Material and Process Engineering, 2006, Dr. Zhang presents a table of describing the oxygen permeability of different materials. The oxygen permeability of dimethylsilicone rubber is indicated as $60*10^9$ in $cm^3*cm/(s*cm^2*cmHg)$, nylon 6 is indicated as $0.004*10^9$, polyethylene terephthalate (PET) is indicated as $0.0019*10^9$, and polytetrafluoroethylene (PTFE) is indicated as $0.0004*10^9$. The permeability of dimethylsilicone rubber to carbon dioxide is indicated as 323. Thus, silicone rubber tends to be porous to substances of interest in monitoring kidney function, while nylon 6, PET and PTFE tend to be substantially non-permeable to substances of interest in monitoring kidney function. However, the flexibility elasticity, and low cost make silicone rubber an attractive material for constructing Foley catheters.

In one example, according to the techniques of this disclosure, a medical device, such as a catheter, may be constructed of a plurality of materials. One of the materials may be silicone rubber. Another of the materials may be one that is substantially non-permeable to a substance of interest, such as, but not limited to carbon dioxide or oxygen. By constructing a medical device, such as a Foley catheter, with a relatively thin layer of a substantially non-permeable material to a substance of interest, such as nylon, PET or PTFE, disposed on a body material (e.g., silicone rubber), degradation of the substance of interest during transit through the medical device may be mitigated or introduction of contaminants into the fluid in the medical device may be mitigated without substantially affecting the flexibility of the medical device. In one example, the thin layer of substantially non-permeable material may be placed on the inner surface of a lumen defined by the medical device and through which a fluid of interest flows from a proximal portion of the medical device to a distal portion. In another example, the thin layer of the substantially non-permeable material may be placed on the outer surface of the medical device.

Certain parameters of urine or other fluids of interest are better measured at the proximal portion of a catheter, such as temperature and pressure. Measuring temperature at the distal portion may lead to relatively inaccurate measurements as the urine may experience heat exchange with the lumen, surrounding tissue and atmosphere while traveling from the proximal portion to the distal portion of the medical device. Measuring pressure at the distal portion may also lead to inaccurate measurements as the distal portion may be higher or lower than the abdomen. By measuring temperature and/or pressure at the proximal portion, these issues may be mitigated.

Thus, it may be desirable to have a medical device, such as a Foley catheter, that may be configured to have sensors positioned at both a proximal portion and a distal portion, or distal to a distal end of the medical device, and comprise a material that is substantially non-permeable to a substance of interest. In some examples, the material is substantially non-permeable to oxygen and/or carbon dioxide. In addition, in some examples, sensors positioned at the proximal portion may include a temperature sensor and/or a pressure sensor and/or sensors positioned at the distal portion may include sensors that sense urine output (e.g., flow or volume), urine concentration, amount of dissolved oxygen in the urine (oxygen tension or uPO2), amount of dissolved carbon dioxide in the urine, urine pH, urine color, urine creatinine, and/or motion.

In some examples, at least some of the sensors are attached directly to the elongated body or to a hub connected to a distal end of the elongated body. In addition to or instead of attaching the sensors to the elongated body or the hub, in some examples, at least one sensor may be attached to a pull wire or push wire of the medical device used to deploy an anchoring member.

Figure 1:
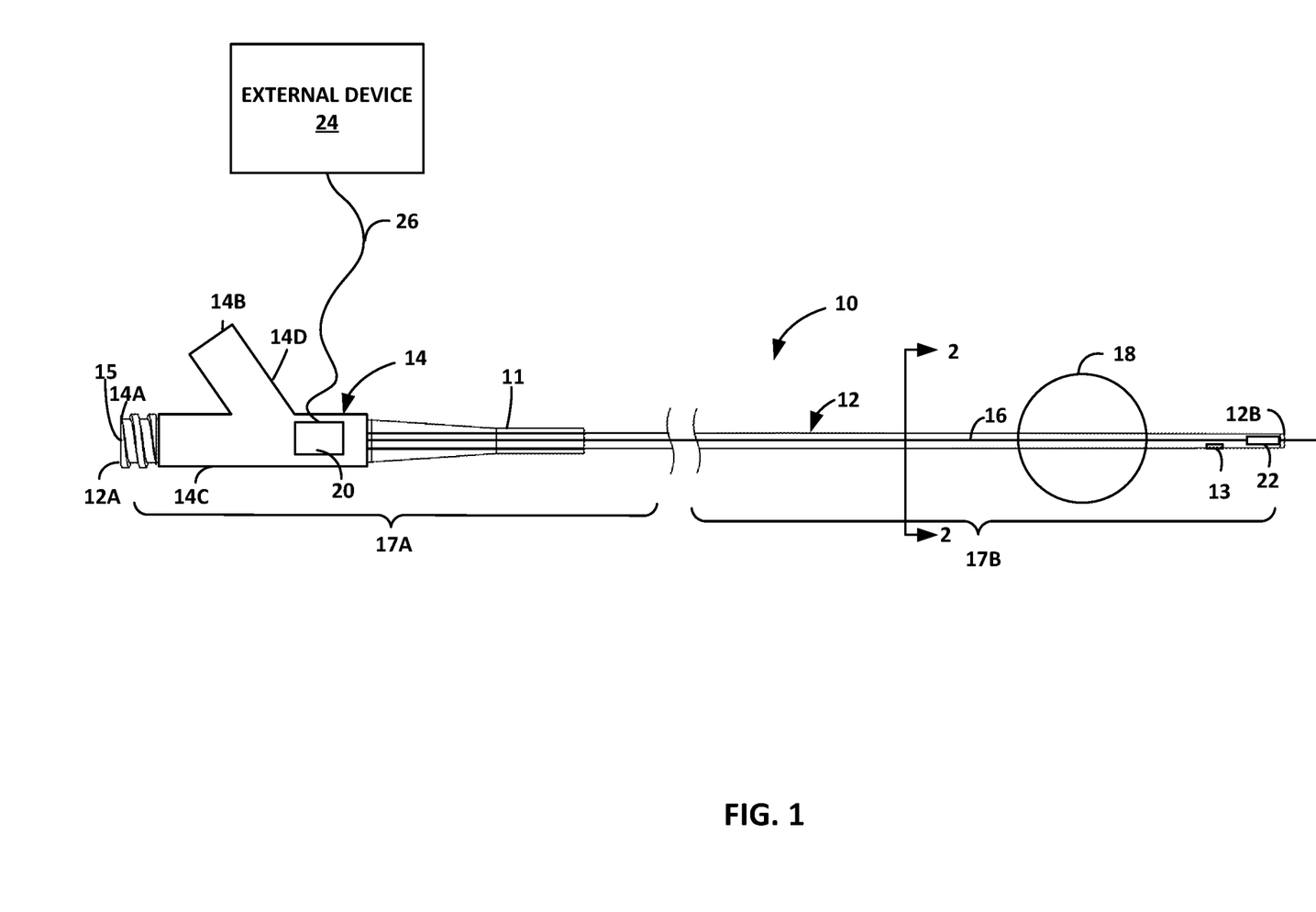
FIG. 1 is a diagram illustrating an example medical device including first and second sensors.

FIG. 1 is a conceptual side elevation view of an example medical device 10, which includes elongated body 12, hub 14, and anchoring member 18. In some examples, medical device 10 is a catheter, such as a Foley catheter. While a Foley catheter and its an intended use is primarily referred to herein to describe medical device 10, in other examples, medical device 10 can be used for other purposes, such as to drain wounds or for intravascular monitoring or medical procedures. Thus, in some instances, medical device 10 can be generally referred to as a catheter.

Medical device 10 includes a distal portion 17A and a proximal portion 17B. Distal portion 17A includes a distal end 12A of elongated body 12 and is intended to be external to a patient's body when in use, while proximal portion 17B includes a proximal end 12B of elongated body 12 and is intended to be internal to a patient's body when in use. For example, when proximal portion 17B is positioned within a patient, e.g., such that proximal end 12B of elongated body 12 is within the patient's urethra or bladder, distal portion 17A may remain outside of the body of the patient.

Elongated body 12 is a body that extends from distal end 12A to proximal end 12B and defines one or more inner lumens. In the example shown in FIGS. 1-2B, elongated body 12 defines lumen 34 and lumen 36 (shown in FIGS. 2A and 2B). In some examples, lumen 34 may be a drainage lumen for draining a fluid from a target site, such as a bladder. In other examples lumen 34 may be used for any other suitable purpose, such as to deliver a substance or another medical device to a target site within a patient. Lumen 34 may extend from fluid opening 13 to fluid opening 14A. Both fluid opening 13 and fluid opening 14A may be fluidically coupled to lumen 34, such that a fluid may flow from one of fluid opening 13 or fluid opening 14A to the other of fluid opening 13 or fluid opening 14A through lumen 34. In the example where lumen 34 is a drainage lumen, fluid opening 13 and fluid opening 14A may be drainage openings. In the example shown in FIG. 1, distal end 12A of elongated body 12 is received within hub 14 and is mechanically connected to hub 14 via an adhesive, welding, or another suitable technique or combination of techniques.

In some examples, elongated body 12 has a suitable length for accessing the bladder of a patient through the urethra. The length may be measured along central longitudinal axis 16 of elongated body 12. In some examples, elongated body 12 may have an outer diameter of about 12 French to about 14 French, but other dimensions may be used in other examples. Distal and proximal portions of elongated body 12 may each have any suitable length.

Anchoring member 18 is positioned at proximal portion 17B of elongated body 12 and is configured to help secure elongated body 12 relative to an anatomical structure of a patient. For example, anchoring member 18 can be expanded from a collapsed (or contracted) configuration to an expanded configuration within a bladder of a patient to prevent elongated body 12 from inadvertent dislodgment from the bladder (e.g., moving distally out of the bladder). Anchoring member 18 can include any suitable structure configured to expand from a relatively low profile collapsed configuration (e.g., to aid placement of catheter 10 in a body of a patient) to a relatively higher profile expanded configuration. For example, anchoring member 18 can include a balloon expandable structure or a non-balloon expandable structure (an expandable structure that is not a balloon), such as, but not limited to, an expandable basket, expandable wings, or expandable mushroom shape, that extends radially away from elongated body 12 in an expanded configuration, or the like. An example of a non-balloon expandable structure is a Malecot-style anchoring member, which includes wings or other structures that extend away from elongated body 12 in an expanded configuration.

In some examples in which anchoring member 18 includes a balloon, fluid opening 13 is positioned proximal to anchoring member 18 as shown in FIG. 1. In other examples, however, fluid opening 13 can be positioned distal to the balloon. In addition, in some examples in which anchoring member 18 includes a non-balloon expandable structure, fluid opening 13 can be positioned proximal to anchoring member 18 as shown in FIG. 1. In other examples, however, fluid opening 13 can be positioned distal to the expandable structure. In some cases, an expandable structure that is not a balloon can have a smaller length (measured along a longitudinal axis of elongated body 12) without compromising an ability of anchoring member 18 to secure elongated body 12 relative to an anatomical structure of a patient. This can enable fluid opening 13 to be positioned more distally, and, therefore, enable a catheter 10 including an anchoring member 18 that includes an expandable structure that is not a balloon to allow for more complete drainage of a bladder of a patient. More complete drainage of the bladder may enable sensors 20, 22 to sense a larger volume of urine during a particular time period, which can increase the response time with which processing circuitry of external device 24 or another device detects changes in the substances sensors 20, 22 monitor in the urine.

Hub 14 is positioned at a distal end of elongated body 12 and defines an opening through which the one or more inner lumens (e.g., lumen 34 shown in FIGS. 2A and 2B) of elongated body 12 may be accessed and, in some examples, closed. While hub 14 is shown in FIG. 1 as having two arms, 14C and 14D, (e.g., a "Y-hub"), hub 14 may have any suitable number of arms, which may depend on the number of inner lumens defined by elongated body 12. For example, each arm may be fluidically or otherwise coupled to a respective inner lumen of elongated body 12. In the example of FIG. 1, hub 14 comprises a fluid opening 14A, which is fluidically coupled to lumen 34, and an anchor deployment opening 14B, which is fluidically or otherwise coupled to an anchor deployment lumen, e.g. lumen 36, (shown in FIGS. 2A and 2B) of elongated body 12. In the example of FIG. 1, lumen 36 may be referred to as an inflation lumen and is configured to deliver an inflation fluid to anchoring member 18 to expand anchoring member 18 to an expanded configuration.

In examples in which anchoring member 18 is a non-balloon expandable structure (e.g., examples of FIGS. 4A-5A), rather than defining an inflation lumen, elongated body 12 may define an anchor deployment lumen configured to receive a deployment mechanism (e.g., a pull wire or a push wire) configured to cause anchoring member 18 to expand and contract in response to a distal or proximal pulling force or pushing force applied to the deployment mechanism. In some of these examples, hub 14 may comprise fluid opening 14A and an anchor deployment opening 14B via which a clinician may access the deployment mechanism.

In examples in which medical device 10 is a Foley catheter, a fluid collection container (e.g., a urine bag) may be attached to fluid opening 14A for collecting urine draining from the patient's bladder. Anchor deployment opening 14B may be operable to connect to an inflation device to inflate anchoring member 18 positioned at proximal portion 17B of medical device 10 or to provide access to an anchor deployment mechanism, such as a pull wire or a push wire. Anchoring member 18 may be uninflated or undeployed when not in use. Hub 14 may include connectors, such as connector 15, for connecting to other devices, such as the fluid collection container or an inflation source in the case where anchoring member 18 is a balloon. In some examples, medical device 10 includes strain relief member 11, which may be a part of hub 14 or may be separate from hub 14.

Proximal portion 17B of medical device 10 comprises anchoring member 18, fluid opening 13, and first sensor 22. Anchoring member 18 may include any suitable structure configured to expand from a relatively low profile state to an expanded state in which anchoring member 18 may engage with tissue of a patient (e.g., inside a bladder) to help secure and prevent movement of proximal portion 17B out of the body of the patient. For example, anchoring member 18 can include an anchor balloon, a non-balloon anchoring structure, such as an expandable basket, expandable wings, expandable mushroom shape or other expandable structure. When inflated or deployed, anchoring member 18 may function to anchor medical device 10 to the patient, for example, within the patient's bladder. In this manner, the portion of medical device 10 on the proximal side of anchoring member 18 may not slip out of the patient's bladder. Fluid opening 13 may be positioned at the surface of longitudinal axis of medical device 10 between anchoring member 18 and the proximal end 12B (as shown) or may be positioned at the proximal end 12B.

First sensor 22 may include one or more sensors that are configured and intended to sense parameters that should be sensed relatively close to the fluid source, such as the bladder, because the parameters may substantially change as a function of time or based on the location at which the parameter is sensed. As discussed above, temperature is one example parameter that may substantially change as a function of time and pressure is one example parameter that may change based on the location at which the parameter is sensed. Thus, temperature and pressure are two parameters that are better sensed at the proximal portion of a catheter (close to the fluid source), and, in some examples, first sensor 22 may comprise sensors such as a temperature sensor and/or pressure sensor. First sensor 22 is configured to communicate sensor data to external device 24 via an electrical, optical, wireless or other connection. In some examples, first sensor 22 may communicate sensor data to external device 24 through a connection(s) within elongated body 12 of medical device 10 from proximal portion 17B to distal portion 17A via wire(s) or optical cable(s). In some examples, the wire(s) may be part of a pull wire or push wire, e.g., configured to move anchoring member 18 from a contracted configuration to an expanded configuration in response to a distal pulling force (away from anchoring member 18) or in response to a proximal pushing force (towards anchoring member 18). In other examples, first sensor 22 may communicate sensor data to external device 24 via a wireless communication technique.

Distal portion 17A of medical device 10 includes second sensor 20. Second sensor 20 may be positioned at hub 14, as shown, or may be positioned elsewhere on distal portion 17A of the body of medical device 10, or may be positioned distal to distal end 12A, e.g., on tubing connected to a fluid collection container (e.g., a urine bag) or the like.

Second sensor 20 includes one or more sensors that are relatively larger, require relatively more electrical or optical connections (e.g., compared to first sensor 22), and/or that sense parameters that may be sensed relatively far away from the fluid source compared to the parameters sensed by first sensor 22. Thus, the one or more parameters second sensor 20 is configured to sense may include parameters that do not substantially change as a function of time or based on the location at which the parameter is sensed. In some examples, second sensor 20 may include sensors configured to sense urine output (e.g., flow or volume), urine concentration, amount of dissolved oxygen in the urine (oxygen tension or uPO2), amount of dissolved carbon dioxide in the urine, urine pH, urine color, urine creatinine, and/or motion.

In some examples, first sensor 22 and/or second sensor 20 are mechanically connected to elongated body 12 or another part of medical device 10 using any suitable technique, such as, but not limited to, an adhesive, welding, by being embedded in elongated body 12, via a crimping band or another suitable attachment mechanism or combination of attachment mechanisms. In some examples, first sensor 22 and/or second sensor 20 are mechanically connected to a deployment mechanism, such as a pull wire or push wire, configured to move anchoring member 18 between expanded and contracted configurations. As discussed above, in some examples, second sensor 20 is not mechanically connected to elongated body 12 or medical device 10, but is instead mechanically connected to a structure that is distal to a distal end of medical device 10, such as to tubing that extends between hub 14 and a fluid collection container.

First sensor 22 and second sensor 20 may be configured to communicate sensor data to an external device 24. External device 24 may be a computing device, such as a workstation, a desktop computer, a laptop computer, a smart phone, a tablet, a server or any other type of computing device that may be configured to receive, process and/or display sensor data. First sensor 22 and second sensor 20 may communicate sensor data to external device 24 via a connection 26. Connection 26 may be an electrical, optical, wireless or other connection. In some examples, first sensor 22 and second sensor 20 may communicate sensor data to external device 24 via different connections.

Although only one first sensor 22 and only one second sensor 20 is shown in FIG. 1, in other examples, medical device 10 can include any suitable number of sensors on proximal portion 17B and any suitable number of sensors on distal portion 17A, where the sensors on proximal portion 17B sense the same or different parameters and the sensors on distal portion 17A sense the same or different parameters. In addition, some or all of the sensors on proximal portion 17B can sense the same or different parameters as the sensors on distal portion 17A. For example, in the case where sensors on the distal portion may be temperature dependent, it may be desirable to sense temperature both on the proximal portion 17B and the distal portion 17A.

Elongated body 12 may be structurally configured to be relatively flexible, pushable, and relatively kink- and buckle-resistant, so that it may resist buckling when a pushing force is applied to a relatively distal portion of the medical device to advance the elongated body proximally through the urethra and into the bladder. Kinking and/or buckling of elongated body 12 may hinder a clinician's efforts to push the elongated body proximally.

As some substances of interest may dissipate from or permeate into a fluid, such as urine, within a lumen 34 of elongated body 12 of medical device 10, elongated body 12 may be constructed to include a material that is substantially non-permeable (e.g., non-permeable or nearly non-permeable) to substances of interest. The material may be positioned to minimize or even prevent the egress of the substance of interest out of lumen 34 via a sidewall of elongated body 12, where the sidewall may be the wall extending between distal end 12A and proximal end 12B. In addition to or instead of minimizing or preventing the egress the substance of interest out of lumen 34 via the sidewall, in some examples, the material may be configured and positioned to minimize or even prevent the ingress of the substance of interest or other contaminants, in some examples, into lumen 34 via the sidewall.

Figure 2A:
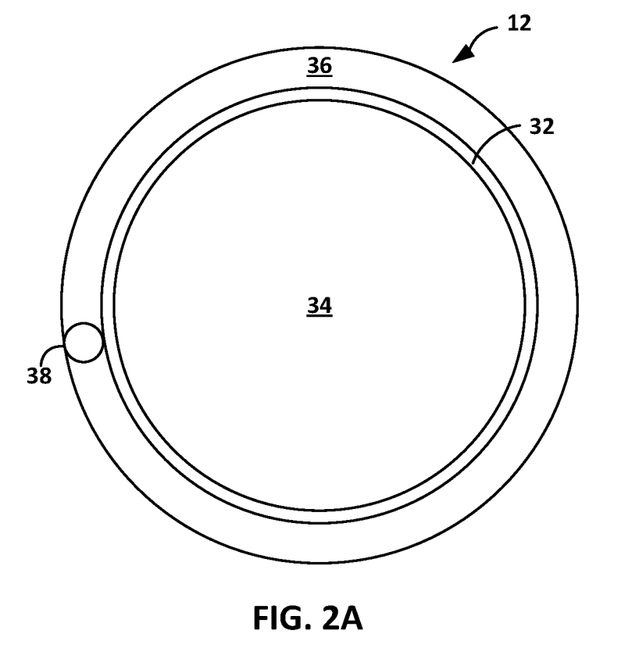
FIGS. 2A and 2B are diagrams illustrating example cross-sections of the medical device of FIG. 1, the cross-sections being take along lines 2-2 of FIG. 1.
Figure 2B:
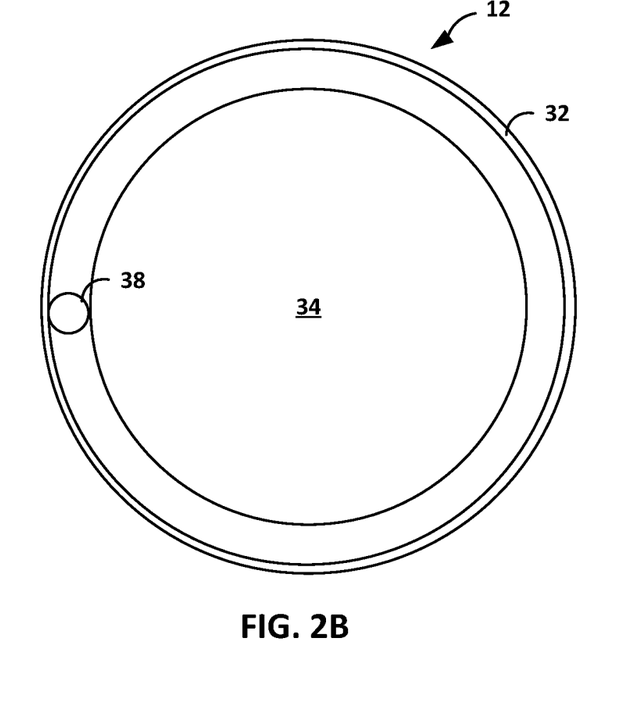

As discussed in further detail relative to FIGS. 2A and 2B, in some examples, a thin layer of the material may be positioned along an inner surface of elongated body 12 that defines lumen 34. In addition to or instead of being on the inner surface, a thin layer of the material may be positioned along an outer surface of elongated body 12. In this manner, the material that is substantially non-permeable to substances of interest may to help minimize or even eliminate degradation and/or contamination of the substances of interest as the fluid in which the substances of interest are present propagates through the lumen of the elongated body to the second sensor 20. In this way, medical device 10 is configured to enable second sensor 20 to sense the substance of interest despite being positioned relatively far away from proximal end 12B of elongated body 12 and the fluid source, such as a bladder.

The thin layer of material may extend from any suitable position on the proximal portion 17B of elongated body 12 to any suitable position on the distal portion 17A of elongated body 12 such that the degradation and/or contamination of substances of interest is inhibited. For example, the thin layer of material may extend from proximal end 12B to distal end 12A. In other examples, the thin layer of material may extend from fluid opening 13 to fluid opening 14A. In other examples, the thin layer of material may extend from fluid opening 13 to second sensor 20.

In some examples, rather than being formed from two or more discrete and separate longitudinally extending segments that are mechanically connected to each other, e.g., at axial butt joints, elongated body 12 may be substantially continuous along a length of elongated body 12. For example, elongated body 12 may include a material that is substantially non-permeable to substances of interest that may form an inner liner that defines a lumen of elongated body 12 (such as lumen 34 of FIGS. 2A-2B) and continuously extends from distal portion 17A to proximal portion 17B of elongated body 12. A substantially continuous elongated body 12 may be better configured to distribute forces in a longitudinal direction (in a direction along longitudinal axis 16) and rotational direction (rotation about longitudinal axis 16) compared to an elongated body including two or more longitudinally extending segments that are mechanically connected to each other. Thus, the substantially continuous construction of elongated body 12 may contribute to the ability of elongated body 12 to transfer axial pushing forces from distal portion 17A of elongated body 12 to proximal portion 17B, as well transfer rotational forces (if any) applied from distal portion 17A of elongated body 12 to proximal portion 17B.

In some examples, at least a portion of an outer surface of elongated body 12 includes one or more coatings, such as an anti-microbial coating, and/or a lubricating coating. The lubricating coating may be configured to reduce static friction and/kinetic friction between elongated body 12 and tissue of the patient as elongated body 12 is advanced through the urethra.

FIGS. 2A and 2B are diagrams illustrating example cross-sections of medical device 10, where the cross-section is taken along line 2-2 in FIG. 1 in a direction orthogonal to central longitudinal axis 16. FIG. 2A depicts a cross section of elongated body 12, which defines lumen 34 and lumen 36. In some examples, lumen 34 may be referred to as a drainage lumen, such as in examples in which medical device 10 is a Foley catheter configured to drain urine from a bladder of a patient, and lumen 36 may referred to as a anchor deployment lumen for deploying an anchoring member, such as anchoring member 18. In some examples, lumen 36 may be referred to as an inflation lumen in examples in which lumen 36 is configured to deliver an inflation fluid to anchoring member 18. In some examples, elongated body 12 may additionally enclose connection 38.

Lumen 34 may serve as a passage for urine entering medical device 10 through fluid opening 13 to fluid opening 14A. In the example shown in FIG. 2A, layer of material 32 that is relatively non-permeable to substances of interest, such as oxygen and/or carbon dioxide, is positioned along an inner surface of elongated body 12 that defines lumen 34. In some examples, material 32 extends along an entire length of lumen 34, while in other examples, material 32 only extends along only a part of a length of lumen 34, for example, from a portion of lumen 34 intended to be in a patient's bladder during use to second sensor 20, which may help maintain a desired level of flexibility of elongated body 12. In addition, as shown in FIG. 2A, in some examples, material 32 extends around an entire inner perimeter of lumen 34 (e.g., an inner circumference in examples in which the inner perimeter is circular in cross-section).

Material 32 is selected based on the one or more substances of interest for which it is desirable to limit outflow out of elongated body 12 or inflow into elongated body 12. In some examples, material 32 may be one or more of nylon, PET, or PTFE.

In some examples, the layer of material 32 is relatively thin, where the thickness of layer of material 32 is measured in a direction orthogonal to longitudinal axis 16, e.g., in a radial direction. For example, the layer of the material may be in the range of 0.001 to 0.100 inches. By keeping the layer of material 32 relatively thin, medical device 10 may remain relatively flexible. While lumen 34 is shown in a particular configuration and shape, lumen 34 and lumen 36 may be of any shape or configuration. In some examples, lumen 34 may be positioned at or near the center of elongated body 12 when viewed as a cross section. In some examples, there may be a plurality of lumens of a same type, for example, a plurality of drainage lumens.

Figure 4A:
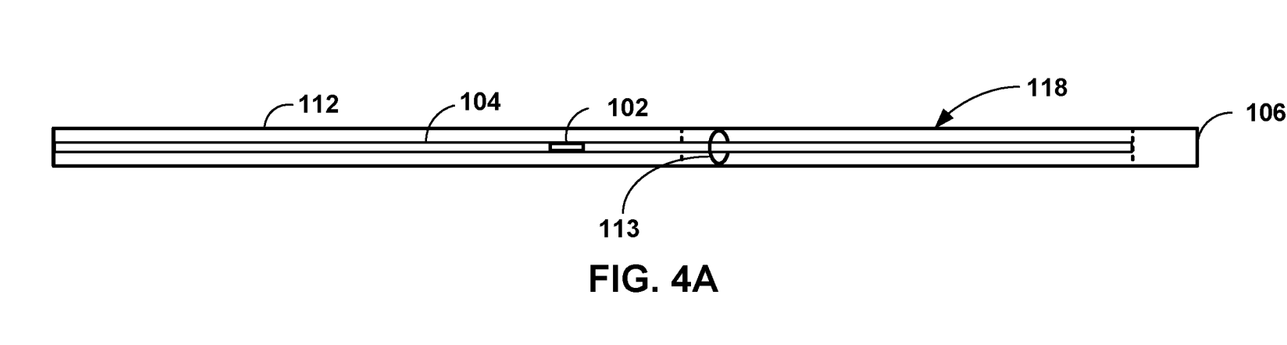
FIGS. 4A-4C are conceptual diagrams of a proximal portion of an example medical device including an anchoring member including a non-balloon expandable structure.
Figure 4B:
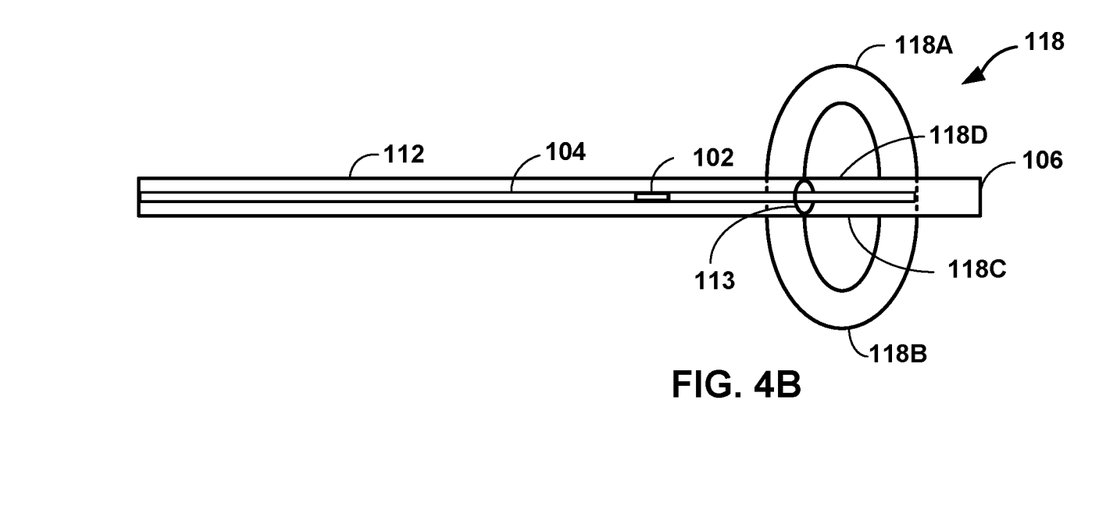
Figure 4C:
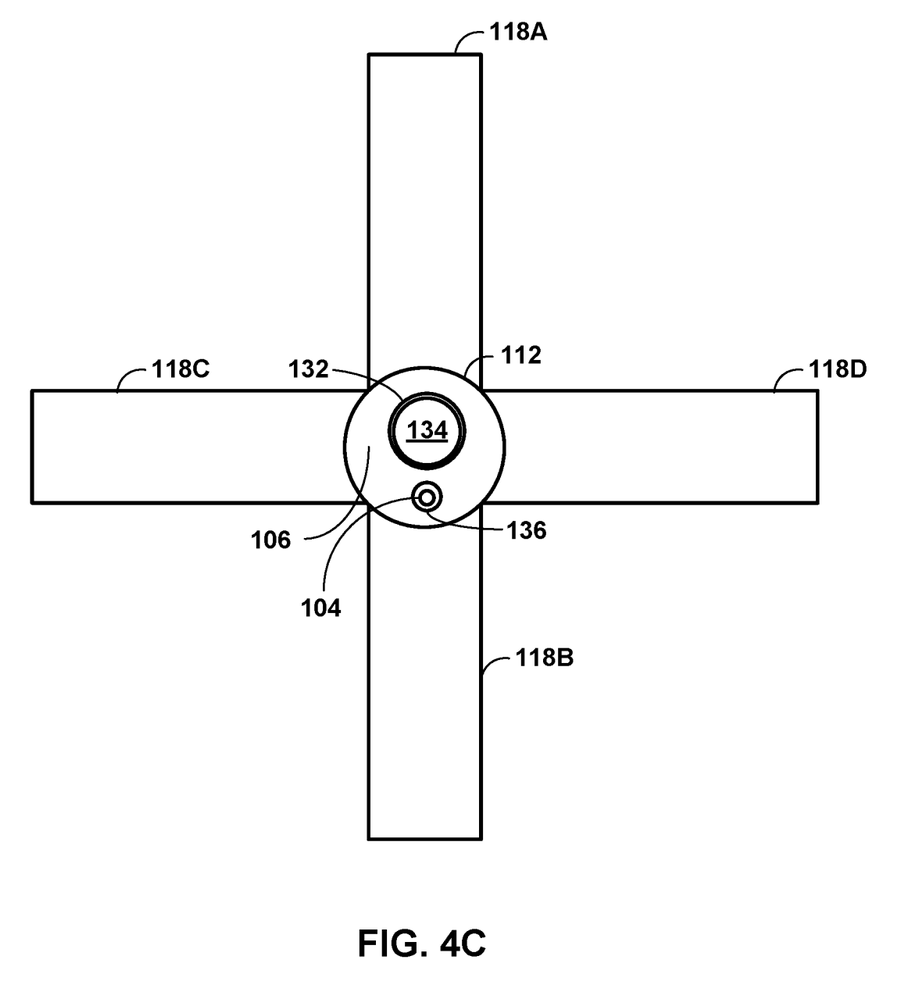
Figure 5A:
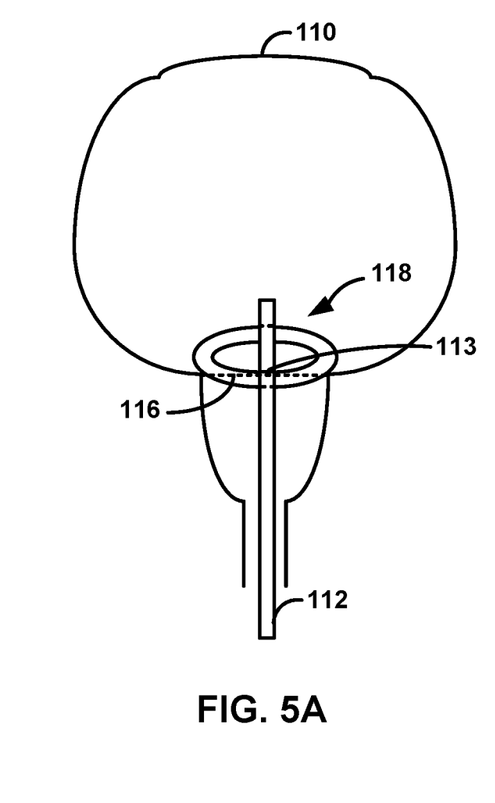
FIGS. 5A and 5B are conceptual diagrams of example catheters with different anchoring members deployed within bladders of patients.

Lumen 36 may serve as a passage for a fluid, such as sterile water or saline, or a gas, such as air, from anchor deployment opening 14B to anchoring member 18. For example, an inflation device (not shown) may pump fluid or gas into lumen 36 through anchor deployment opening 14B into anchoring member 18 such that anchoring member 18 is inflated to a size suitable to anchor medical device 10 to the patient's bladder. While lumen 36 is shown in a particular configuration and shape, lumen 36 may be of any configuration or shape. In some examples, there may be a plurality of lumens for deploying anchoring member 18. For example, a plurality of anchor deployment lumens may substantially surround lumen 34. In some examples, anchoring member 18 may be an expandable structure that is not an inflatable balloon. For example, anchoring member 18 may be an expandable basket, expandable wings (such as shown in FIGS. 4 and 5A), expandable mushroom shape, or other expandable structure. In such examples, lumen 36 may include a deployment mechanism which may permit a clinician to expand the expandable structure. For example, lumen 36 may include a mechanical device (such as a pull wire or push wire) that may be pushed and pulled separately from the medical device 10 by a clinician to expand or retract the expandable structure.

In some examples, connection 38 may serve to connect first sensor 22 positioned at proximal portion 17B to connection 26. Connection 38 may be an electrical, optical or other connection. In some examples, connection 38 may comprise a plurality of connections. For example, connection 38 may include one of more wired or optical connections to a temperature sensor and one or more connections to a pressure sensor. In some examples, connection 38 may include one or more power connections to power first sensor 22 and one or more communications connections to receive sensor data from first sensor 22. In other examples, first sensor 22 may be connected to external device 24 via a pull wire or push wire.

FIG. 2B is another example of a cross-section of elongated body 12. The example of FIG. 2B is similar to FIG. 2A, however, the layer of material 32 is not surrounding an inner perimeter of lumen 34, but is instead surrounding an outer surface of elongated body 12. Layer of material 32 can be, for example, an outermost surface of elongated body 12 or may be covered by another material, such as a lubricious coating. In other examples, layer of material 32 can be a middle layer of the wall of elongated body 12, e.g., positioned between structural layers of silicone rubber or another suitable flexible material.

As in FIG. 2A, material 32 may be relatively non-permeable to substances of interest, such as oxygen and/or carbon dioxide. In some examples, material 32 may be nylon, PET, or PTFE. In some examples the layer of material 32 is relatively thin. For example, the layer of material 32 may be in the range of 0.001 to 0.100 inches. By keeping the layer of material 32 relatively thin, medical device 10 may remain flexible. In some examples, material 32 extends along an entire length of elongated body 12 from distal end 12A to proximal end 12B, while in other examples, material 32 only extends along part of a length of elongated body 12.

In addition, in some examples, material extends around an entire outer perimeter of elongated body 12, while in other examples, material 32 extends around less than an entire perimeter of elongated body 12, such as about 90% or more of the entire perimeter of elongated body 12, which may help maintain a desired level of flexibility of elongated body 12.

Figure 3:
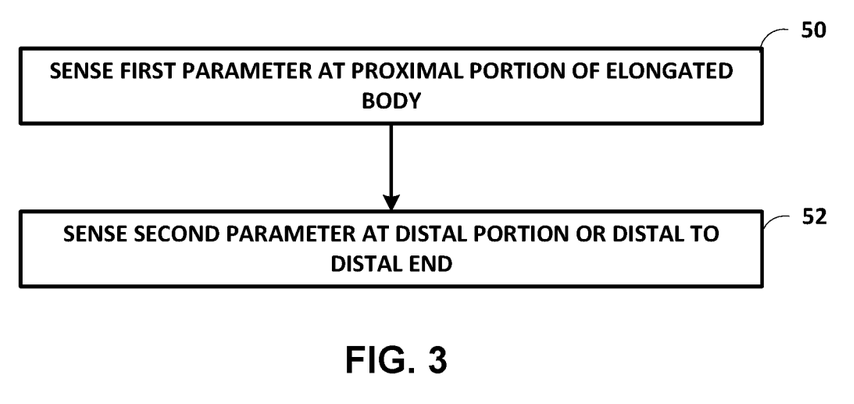
FIG. 3 is a flowchart illustrating an example method of operating a medical device.

FIG. 3 is a flowchart illustrating an example operation of medical device 10. A clinician may insert proximal end 12B of medical device 10 into a patient's urethra. The clinician may also advance medical device 10 through the patient to a target site, e.g., until uninflated or undeployed anchoring member 18 is within the patient's bladder. In the case where anchoring member 18 is a balloon, the clinician may connect anchor deployment opening 14B to an inflation device. The clinician may connect opening 14A to a fluid collection container and/or to external sensors. The clinician may deploy anchoring member 18 to help secure medical device 10 relative to the target site. For example, the clinician may inflate anchoring member 18, for example, using an inflation device and inflation fluid, such as sterile water, saline, or a gas. In examples in which anchoring member 18 is a non-balloon expandable structure, such as an expandable basket, expandable wings, expandable mushroom shape or other expandable structure, the clinician may deploy anchoring member 18 by pushing a structure, such as a push wire, radially outwards or pulling back on a structure, such as a pull wire, to cause the expandable structure to expand radially outwards.

First sensor 22, positioned at proximal portion 17B of elongated body 12 may sense a first parameter such as temperature and/or pressure within the patient's bladder (50). Lumen 34 may transport urine from the proximal portion 17B of medical device 10 to the distal portion 17A of medical device 10. Second sensor 20, positioned at distal portion 17A or distal to distal end 12A may sense a second parameter, the second parameter comprising a substance of interest in a fluid in lumen 34, (52). For example, second sensor 20 may physically contact urine flowing through lumen 34 and may sense a second parameter such as urine output (e.g., flow or volume), urine concentration, amount of dissolved oxygen in the urine, amount of dissolved carbon dioxide in the urine, urine pH, urine color, urine creatinine, and/or motion. In some examples, second sensor 20 may sense urine between medical device 10 and a fluid collection container or in the fluid collection container.

While the example of FIG. 3, sets forth a number of steps, these steps may be performed in a different order or concurrently. For example, the clinician may connect fluid opening 14A to a fluid collection container and/or to external sensors prior to inserting the proximal end 12B of medical device 10 into the patient's urethra and lumen 34 may transport urine concurrently with first sensor 22 and/or second sensor 20 sensing the fluid.

As discussed above, in some examples anchoring member 18 may include a non-balloon expandable structure. Traditional Foley catheters use a balloon anchoring member that is inflated within the bladder to provide an anchor to prevent the catheter from inadvertently dislodging. Typically, the fluid opening for the urine (e.g., fluid opening 13) is positioned proximal to the balloon (e.g., anchoring member 18) as shown in FIG. 1. In this configuration, the urine in the bladder needs to rise to the level of the fluid opening to be evacuated.

In some examples, a non-balloon expandable structure, such as an expandable basket, expandable wings, expandable mushroom shape, or other expandable structure. One example of a non-balloon expandable structure is a Malecot-style expandable structure. A non-balloon anchoring member may be utilized as anchoring member 18 as an alternative to or in addition to a balloon anchoring member. FIGS. 4A-4C are conceptual diagrams of a proximal portion of an example medical device having an example non-balloon expandable structure anchoring member at a proximal portion of an elongated body 112. Elongated body 112 is an example of elongated body 12 of FIG. 1 and defines fluid opening 113 distal to a proximal end 106 of elongated body 112. FIG. 4A shows a non-balloon expandable structure anchoring member 118 (the portion of elongated body 112 between the dashed lines) in an undeployed, contracted configuration. In some examples, when anchoring member 118 is in the undeployed position, fluid opening 113 is largely blocked by anchoring member 118.

The example medical device of FIGS. 4A-4C includes pull wire 104 (or alternatively a push wire or other deployment mechanism) mechanically connected to anchoring member 118 or to elongated body 112. Pull wire 104 may run from the proximal portion of elongated body 112, e.g., through an anchor deployment lumen, and through anchor deployment opening 14B (FIG. 1) with sufficient length distal to anchor deployment opening 14B to permit a clinician to pull on pull wire 104. In some examples, a distal end of pull wire 104 may include a mechanism to prevent pull wire 104 from completely entering anchor deployment lumen 136 (not shown in FIGS. 4A-4B for simplicity purposes but shown in FIG. 4C). In some examples, anchoring member 118 is configured to expand radially outward away from an outer surface of elongated body 112 in response to a distal pulling force applied to pull wire 104. For example, the clinician may pull on a portion of pull wire 104 distal to anchor deployment opening 14B or pull wire 104 can be coupled to a slider or thumbwheel that can be actuated by the clinician to apply the distal pulling force to pull wire 104. In these examples, the force of pulling on pull wire 104 causes the wings of anchoring member 118 to split apart from each other, e.g., as proximal end 106 of elongated body 12 is drawn in the distal direction or as a portion of anchoring member 118 is more directly drawn in the distal direction by pull wire 104.

In FIGS. 4B and 4C, anchoring member 118 is shown in the deployed position. Anchoring member 118 may include wings, such as wing 118A, wing 118B, wing 118C, and wing 118D. Fluid opening 113 may be exposed when the wings split apart from each other when deployed. While in the example of FIG. 4B, anchoring member 118 has four wings, any suitable number of wings may be used.

Also shown in FIG. 4C is a layer of material 132 on the perimeter of lumen 134 (internal or external to lumen 134), which may be a drainage lumen. Material 132 may be relatively non-permeable to substances of interest, such as oxygen and/or carbon dioxide. In some examples, material 132 may be nylon, PET, or PTFE. In some examples the layer of material 32 is relatively thin. For example, the layer of material 32 may be in the range of 0.001 to 0.100 inches.

In the example shown in FIG. 4C, pull wire 104 is shown in anchor deployment lumen 136. While the configuration of anchor deployment lumen 136 and lumen 134 are shown in a particular configuration and shape, anchor deployment lumen 136 and lumen 134 may be of any appropriate shape or configuration.

In some examples, the anchoring of anchoring member 118 is passive and the wings 18A-18D are biased to be in a deployed state absent a force pushing wings 18A-18D radially inwards towards the outer surface of elongated body 112. In other words, in these examples, the natural position of wings 18A-18D is extended as shown in FIGS. 4B and 4C. In these examples, wings 18A-18D can be collapsed (e.g., during a procedure in which elongated body 112 is inserted in the bladder) with a relatively stiff stylet inside elongated body 112 that stretches elongated body 112 to cause anchoring member 18 to maintain a lower profile collapsed configuration or by applying a distal pulling force to a pull wire 104. The stylet can be removed to allow deploy anchoring member 18 and cause the wings 18A-18D to extend radially outward. In other examples, wings 18A-18D can be collapsed using an outer sheath that applies a radially inward force to wings 18A-18D. The sheath can be distally withdrawn to deploy anchoring member 18 and cause the wings 18A-18D to extend radially outward.

In other examples, wings 18A-18D may be preferentially undeployed and are configured to maintain a collapsed configuration in the absence of, for example, a pulling force applied to pull wire 134. In the example where the wings are naturally undeployed, the natural position of the wings is unextended, such as the position shown in FIG. 4A. Once the device is inserted into a patient, the wings may be extended by, for example, pulling on pull wire 104 as discussed above. In some examples, pull wire 104 may be attached to wings 118A-118D at one end, such as the proximal side of anchoring member 118 or to elongated body 112 proximal to anchoring member 118.

Pull wire 104 can include any suitable configuration. In some examples, pull wire 104 is formed from a metal, a polymer, or any combination thereof. Pull wire 104 is configured to be held in place, e.g., to keep anchoring member 118 in an expanded state in examples in which wings 18A-18D are preferentially undeployed in an at rest state.

In some examples, pull wire 104 includes sensor 102. Sensor 102 may include one or more of a pressure sensor, a temperature sensor, an accelerometer, or an electrical conductivity sensor. Sensor 102 may be an example of first sensor 22 of FIG. 1 in some examples. Sensor 102 may be physically attached to pull wire 104, e.g., on the proximal portion of the pull wire. For example, sensor 102 may be located relatively close to a proximal end of the pull wire so as to sense parameters such as temperature, pressure or other parameters better sensed at the proximal portion of a catheter. Any wire or optical cable for communicatively coupling sensor 102 to external device 24 may be attached to pull wire 104 as well or may be pull wire 104 itself. For example, one or more sensors, such as sensor 102, may be incorporated into pull wire 104. In some examples, the pull wire may contain elements that may transmit optical or electrical signals from sensor 102. In addition or instead of being attached to pull wire 104, in some examples, sensor 102 may be attached to the wings of anchoring member 118.

In some examples, sensor 102 may be positioned at or near proximal tip 106 of the device. In some examples, anchoring member 118 may have wings only in a single plane (e.g., wings 118A and 118B and not wings 118C and 118D). Such an implementation may still provide sufficient anchoring while decreasing the volume required to anchor proximal end 106 of the medical device in the bladder which may further decrease the amount of retained fluid in the bladder.

Anchoring member 118 shown in FIGS. 4A-4C is one example of a non-balloon expandable structure. In other examples, rather than including wings 118A-118D, anchoring member 118 can include another configuration that enables anchoring member 118 to expand radially outward to help retain elongated body 12 in a bladder or other structure of a patient, such as, but not limited to, an expandable basket, expandable arms that are more linear in an expanded configuration than the example wings 118A-118D shown in FIGS. 4A-4C, and the like. In any of these examples, anchoring member 18 can be configured to enable to flow through the expanded anchoring member 118 to fluid opening 113. In any of these examples, anchoring member 118 can be formed from any suitable material, such as, but not limited to, a polymer, a metal (e.g., nitinol, stainless steel, or the like), or any combination thereof.

Figure 5B:
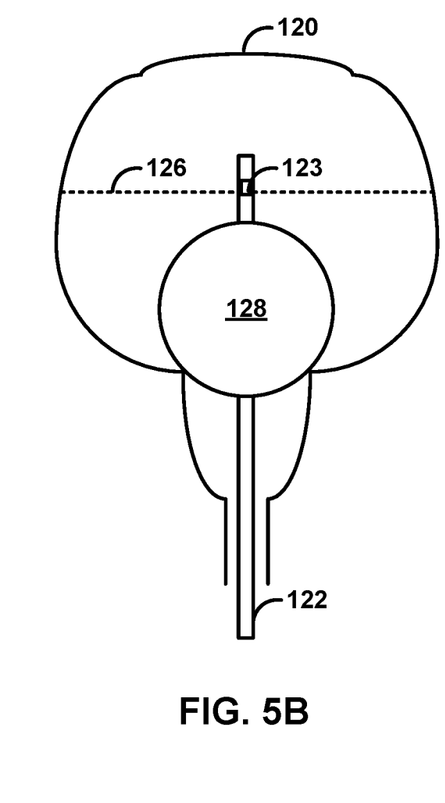

One potential advantage of a non-balloon expandable structure anchoring member on a Foley catheter is that when the anchoring member is in an expanded state, fluid opening 113 sits relatively low in the bladder, allowing for more complete drainage of the bladder. FIGS. 5A and 5B are conceptual diagrams of example catheters with different anchoring members deployed within bladders of patients. FIG. 5A shows an example of the catheter of FIGS. 4A-4C with Melecot-style anchoring member 118 on a proximal portion of elongated body 112 and deployed in an expanded state in bladder 110. FIG. 5B shows an example catheter including an elongated body 122 and a balloon anchoring member 128 at a proximal portion of elongated body 122 and deployed in an expanded, inflated state in bladder 120. Anchoring members 118 and 128 are examples of anchoring member 18 of FIG. 1, and elongated bodies 112, 122 are examples of elongated body 12 of FIG. 1.

In FIG. 5A, fluid opening 113 of elongated body 112 sits lower in bladder 110 than does fluid opening 123 of elongated body 122 in bladder 120. Due to the fluid opening 113 sitting lower than fluid opening 123, urine level 116 in bladder 110 is lower than urine level 126 in bladder 120 after fluid drains from bladder 110, 120, respectively, through the drainage lumen of the respective elongated body 112, 122. More drainage of urine from bladder 110, 120 can help increase a response time with which processing circuitry 200 (FIG. 6) of external device 24 detects changes in the substances being sensed in the urine by, e.g., based on an output from one or both sensors 20, 22 (FIG. 1). The larger the retained volume is, the more the sensed signal is averaged and consequently the longer it may take for processing circuitry 200 to determine a physiologically significant change in the sensed signal. Thus, by utilizing an anchoring member that permits a fluid opening to sit lower in the bladder, such as non-balloon expandable structure anchoring member 118, a sensor such as second sensor 20 that is configured to sense a parameter of interest, such as dissolved oxygen in urine, may more accurately sense the parameter of interest.

Figure 6:
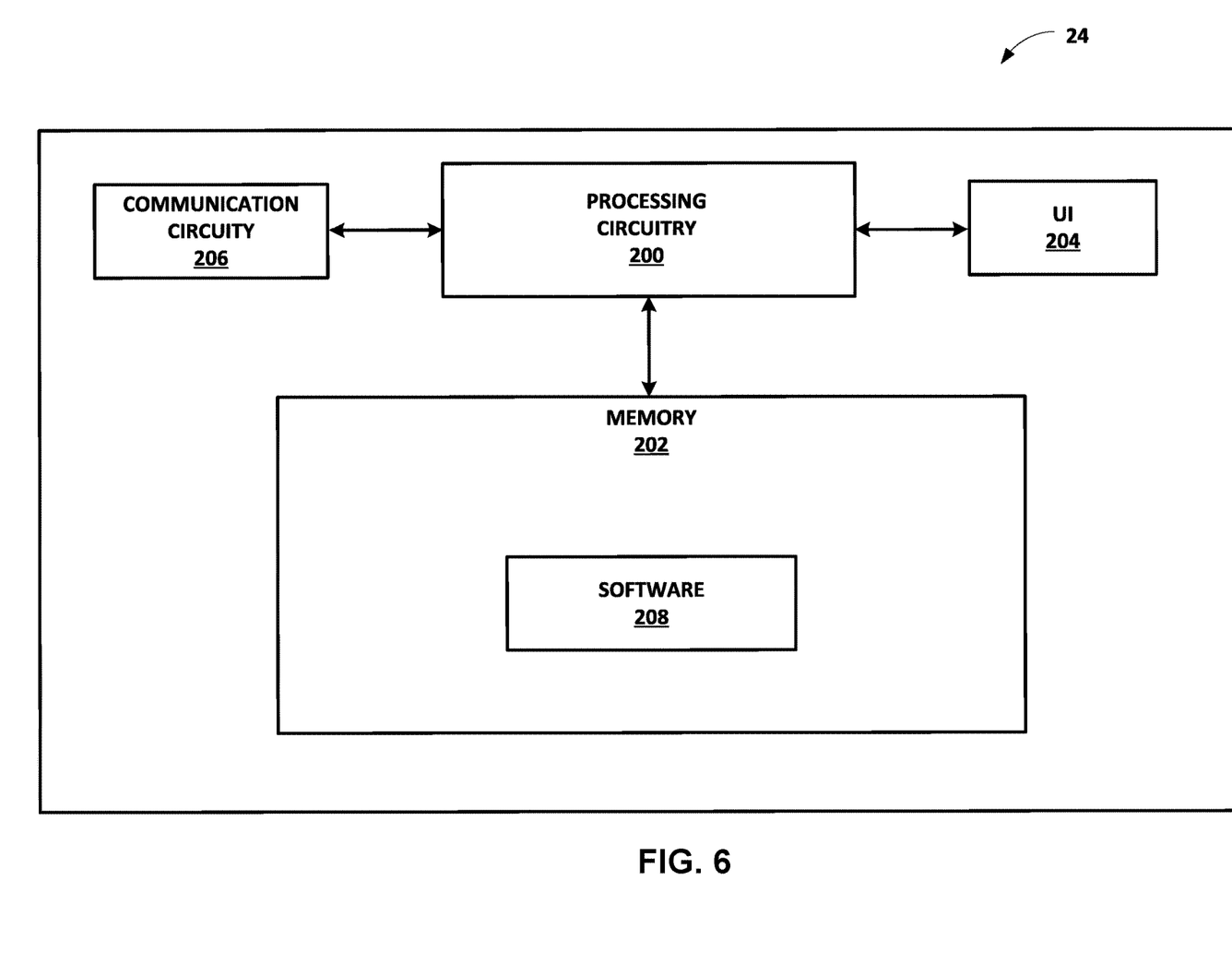
FIG. 6 is a block diagram of an example external device that may be used with a medical device described herein.

FIG. 6 is a functional block diagram illustrating an example of an external device 24 configured to communicate with first sensor 22 and second sensor 20 and receive information from sensors 20, 22. In the example of FIG. 6, external device 24 includes processing circuitry 200, memory 202, user interface (UI) 204, and communication circuitry 206. External device 24 may be a dedicated hardware device with dedicated software for the reading sensor data. Alternatively, external device 24 may be an off-the-shelf computing device, e.g., a desktop computer, a laptop computer, a tablet, or a smartphone running a mobile application that enables external device 24 to read sensor data from first sensor 22 and second sensor 20.

In some examples, a user of external device 24 may be clinician, physician, or heath care giver. In some examples, a user uses external device 24 to monitor a patient's kidney function. In some examples, the user may interact with external device 24 via UI 204, which may include a display to present a graphical user interface to the user, and a keypad or another mechanism (such as a touch sensitive screen) for receiving input from the user. External device 24 may communicate with first sensor 22 and/or second sensor using wired, wireless or optical methods through communication circuitry 206.

Processing circuitry 200 and other processing circuitry described herein may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 and other memory described herein may store program instructions, such as software 208, which may include one or more program modules, which are executable by processing circuitry 200. When executed by processing circuitry 200, such program instructions may cause processing circuitry 200 and external device 24 to provide the functionality ascribed to them herein. The program instructions may be embodied in software and/or firmware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The present disclosure includes the following examples.

Example 1. A device comprising: an elongated body defining a lumen, the elongated body comprising a proximal portion and a distal portion; an anchoring member positioned at the proximal portion of the elongated body; a first sensor positioned at the proximal portion of the elongated body; and a second sensor positioned at the distal portion of the elongated body or distal to a distal end of the elongated body, the second sensor configured to sense a substance of interest, wherein the elongated body comprises a material that is a substantially non-permeable to the substance of interest.

Example 2. The device of example 1, wherein the first sensor comprises at least one of a temperature sensor or a pressure sensor.

Example 3. The device of any combination of examples 1-2, wherein the second sensor comprises at least one of a dissolved gas sensor, a flow sensor, a volume sensor, a pH sensor, a creatinine sensor, a color sensor, or a motion sensor.

Example 4. The device of any combination of any of examples 1-3, wherein the second sensor comprises a dissolved gas sensor comprising at least one of a dissolved oxygen sensor or a dissolved carbon dioxide sensor.

Example 5. The device of any combination of examples 1-4, wherein the material extends from the distal portion to a proximal portion of the elongated body and is configured to minimize a flow of the substance of interest from the lumen to an environment outside the elongated body.

Example 6. The device of any combination of examples 1-5, wherein the material comprises at least one of nylon, polyethylene terephthalate (PET), or polytetrafluoroethylene (PTFE).

Example 7. The device of any combination of examples 1-6, wherein the elongated body comprises a layer of silicone and a layer of the material.

Example 8. The device of any combination of examples 1-7, wherein the substance of interest comprises at least one of oxygen or carbon dioxide.

Example 9. The device of any combination of examples 1-8, wherein the material is disposed on an inner surface of the elongated body, the inner surface defining the lumen.

Example 10. The device of any combination of examples 1-8, wherein the material is disposed on an outer surface of the elongated body.

Example 11. The device of any combination of examples 1-10, wherein the elongated body comprises a Foley catheter.

Example 12. The device of any combination of example 1-11, further comprising a hub at the distal end of the elongated body, wherein the second sensor is positioned at the hub.

Example 13. The device of any combination of example 1-11, further comprising a hub at the distal end of the elongated body, wherein the second sensor is positioned distal to the hub.

Example 14. The device of any combination of examples 1-13, wherein the anchoring member comprises at least one of an inflatable balloon or an expandable structure.

Example 15. The device of example 14, wherein the anchoring member comprises an inflatable balloon.

Example 16. The device of example 14 or 15, wherein the anchoring member comprises a non-balloon expandable structure, the device further comprising a pull wire configured to deploy the non-balloon expandable structure.

Example 17. The device of example 15, wherein the first sensor is positioned on the pull wire.

Example 18. A method comprising: sensing, by a first sensor positioned at a proximal portion of an elongated body of a medical device, a first parameter, the elongated body defining a lumen and the medical device further comprising an anchoring member on the proximal portion; and sensing, by a second sensor positioned at a distal portion of the elongated body or distal to a distal end of the elongated body, a second parameter, the second parameter comprising a substance of interest in a fluid in the lumen, wherein the elongated body comprises a material that is substantially non-permeable to the substance of interest.

Example 19. The method of example 18, wherein the first parameter comprises at least one of a temperature or pressure.

Example 20. The method of any combination of examples 18-19, wherein the second sensor comprises at least one of a dissolved gas sensor, a flow sensor, a volume sensor, a pH sensor, a creatinine sensor, a color sensor, or a motion sensor.

Example 21. The method of any combination of examples 18-20, wherein the second sensor comprises a dissolved gas sensor comprising at least one of a dissolved oxygen sensor or a dissolved carbon dioxide sensor.

Example 22. The method of any combination of examples 18-21, wherein the material extends between the distal end and a proximal end of the elongated body and is configured to minimize a flow of the substance of interest from the lumen to an environment outside the elongated body.

Example 23. The method of any combination of examples 18-22, wherein the material comprises at least one of nylon, polyethylene terephthalate (PET), or polytetrafluoroethylene (PTFE).

Example 24. The method of any combination of examples 18-23, wherein the elongated body comprises a layer of silicone and a layer of the material.

Example 25. The method of any combination of examples 18-24, wherein the substance of interest comprises at least one of oxygen or carbon dioxide.

Example 26. The method of any combination of example 18-25, wherein the material is disposed on an inner surface of the elongated body, the inner surface defining the lumen.

Example 27. The method of any combination of examples 18-25, wherein the material is disposed on an outer surface of the elongated body.

Example 28. The method of any combination of examples 18-27, wherein the elongated body comprises a Foley catheter.

Example 29. The method of any combination of examples 18-28, wherein the medical device further comprises a hub at a distal end of the elongated body, wherein the second sensor is positioned at the hub.

Example 30. The method of any combination of examples 18-29, wherein the medical device further comprises a hub at a distal end of the elongated body, wherein the second sensor is positioned distal to the hub.

Example 31. The method of any combination of examples 18-30, further comprising securing, via the anchoring member on the proximal portion of the elongated body, the medical device to a patient.

Example 32. The method of example 31, wherein the anchoring member is an inflatable balloon.

Example 33. The method of example 32, wherein the anchoring member is a non-balloon expandable structure.

Example 34. A Foley catheter comprising: an elongated body defining a drainage lumen, the elongated body comprising a proximal portion and a distal portion, the proximal portion defining a drainage opening fluidically coupled to the drainage lumen; an anchoring member positioned at the proximal portion of the elongated body; a first sensor positioned at the proximal portion of the elongated body; and a second sensor positioned at the distal portion of the elongated body or distal to a distal end of the elongated body, the second sensor configured to sense a substance of interest, wherein the elongated body comprises a material that is a substantially non-permeable to the substance of interest, the material extending from the drainage opening to the second sensor.

Example 35. The Foley catheter of example 34, wherein the material comprises at least one of nylon, PET, or PTFE.

Example 36. The Foley catheter of example 34 or 35, wherein the anchoring member is an inflatable balloon.

Example 37. The Foley catheter of any combination of examples 34-36, wherein the anchoring member is a non-balloon expandable structure.

Various examples have been described. These and other examples are within the scope of the following claims.

What is claimed is:

1. A device comprising:
    an elongated body defining a lumen, the elongated body comprising a proximal portion and a distal portion, wherein the proximal portion is configured to be inserted into a patient and the distal portion is configured to remain outside the patient when the proximal portion is inserted into the patient;
    an anchoring member positioned at the proximal portion of the elongated body;
    a first sensor positioned at the proximal portion of the elongated body; and
    a second sensor positioned at the distal portion of the elongated body or distal to a distal end of the elongated body, the second sensor configured to sense a substance of interest,
    wherein the elongated body comprises a material that is a substantially non-permeable to the substance of interest.

2. The device of claim 1, wherein the first sensor comprises at least one of a temperature sensor or a pressure sensor.

3. The device of claim 1, wherein the second sensor comprises at least one of a dissolved gas sensor, a flow sensor, a volume sensor, a pH sensor, a creatinine sensor, a color sensor, or a motion sensor.

4. The device of claim 3, wherein the second sensor comprises the dissolved gas sensor comprising at least one of a dissolved oxygen sensor or a dissolved carbon dioxide sensor.

5. The device of claim 1, wherein the material extends from the distal end to a proximal end of the elongated body and is configured to minimize a flow of the substance of interest from the lumen to an environment outside the elongated body.

6. The device of claim 1, wherein the material comprises at least one of nylon, polyethylene terephthalate (PET), or polytetrafluoroethylene (PTFE).

7. The device of claim 1, wherein the elongated body comprises a layer of silicone and a layer of the material.

8. The device of claim 1, wherein the substance of interest comprises at least one of oxygen or carbon dioxide.

9. The device of claim 1, wherein the material is disposed on an inner surface of the elongated body, the inner surface defining the lumen.

10. The device of claim 1, wherein the material is disposed on an outer surface of the elongated body.

11. The device of claim 1, wherein the elongated body comprises a Foley catheter.

12. The device of claim 1, further comprising a hub at the distal end of the elongated body, wherein the second sensor is positioned at the hub.

13. The device of claim 1, wherein the anchoring member comprises at least one of an inflatable balloon or a non-balloon expandable structure.

14. The device of claim 13, wherein the anchoring member comprises the non-balloon expandable structure, the device further comprising a pull wire configured to deploy the non-balloon expandable structure.

15. The device of claim 14, wherein the first sensor is positioned on the pull wire.

16. A method comprising:
    sensing, by a first sensor positioned at a proximal portion of an elongated body of a medical device, a first parameter, the elongated body defining a lumen and the medical device further comprising an anchoring member positioned at the proximal portion, when the proximal portion is in a patient; and
    sensing, by a second sensor positioned at a distal portion of the elongated body or distal to a distal end of the elongated body, a second parameter, the second parameter comprising a substance of interest in a fluid in the lumen, wherein when the proximal portion is in the patient, the distal portion remains outside the patient;
    wherein when the elongated body comprises a material that is substantially non-permeable to the substance of interest.

17. The method of claim 16, wherein the first parameter comprises at least one of a temperature or pressure.

18. The method of claim 16, wherein the second sensor comprises at least one of a dissolved gas sensor, a flow sensor, a volume sensor, a pH sensor, a creatinine sensor, a color sensor, or a motion sensor.

19. The method of claim 18, wherein the second sensor comprises the dissolved gas sensor comprising at least one of a dissolved oxygen sensor or a dissolved carbon dioxide sensor.

20. The method of claim 16, wherein the material extends between the distal end and a proximal end of the elongated body and is configured to minimize a flow of the substance of interest from the lumen to an environment outside the elongated body.

21. The method of claim 16, wherein the material comprises at least one of nylon, polyethylene terephthalate (PET), or polytetrafluoroethylene (PTFE).

22. The method of claim 16, wherein the elongated body comprises a layer of silicone and a layer of the material.

23. The method of claim 16, wherein the substance of interest comprises at least one of oxygen or carbon dioxide.

24. The method of claim 16, wherein the elongated body comprises a Foley catheter.

25. The method of claim 16, wherein the medical device further comprises a hub at the distal end of the elongated body, wherein the second sensor is positioned at the hub.

26. A Foley catheter comprising:
 an elongated body defining a drainage lumen, the elongated body comprising a proximal portion and a distal portion, the proximal portion defining a drainage opening fluidically coupled to the drainage lumen, wherein the proximal portion is configured to be inserted into a patient and the distal portion is configured to remain outside the patient when the proximal portion is inserted into the patient;
 an anchoring member positioned at the proximal portion of the elongated body;
 a first sensor positioned at the proximal portion of the elongated body; and
 a second sensor positioned at the distal portion of the elongated body or distal to a distal end of the elongated body, the second sensor configured to sense a substance of interest,
 wherein the elongated body comprises a material that is a substantially non-permeable to the substance of interest, the material extending from the drainage opening to the second sensor.

27. The Foley catheter of claim 26, wherein the anchoring member is an inflatable balloon.

28. The Foley catheter of claim 26, wherein the anchoring member is a non-balloon expandable structure.

* * * * *